United States Patent [19]

Farge et al.

[11] 4,423,214
[45] * Dec. 27, 1983

[54] 3-VINYLCEPHALOSPORIN DERIVATIVES

[75] Inventors: Daniel Farge; Pierre L. Roy, both of Thiais; Claude Moutonnier, Le Plessis Robinson; Jean-François Peyronel, Palaiseau, all of France

[73] Assignee: Rhone-Poulenc Industries, Paris, France

[*] Notice: The portion of the term of this patent subsequent to Dec. 22, 1998, has been disclaimed.

[21] Appl. No.: 322,949

[22] Filed: Nov. 19, 1981

[30] Foreign Application Priority Data

Nov. 20, 1980 [FR] France ................. 80 24634

[51] Int. Cl.³ .................................... C07D 501/24
[52] U.S. Cl. .................................... 544/22; 542/420; 542/437
[58] Field of Search .................. 544/22; 542/420, 437

[56] References Cited

U.S. PATENT DOCUMENTS 4,278,793 9/1981 Durckheimer et al. ............. 544/27
4,307,233 12/1981 Farge et al. ......................... 544/29

Primary Examiner—Paul M. Coughlan, Jr.
Attorney, Agent, or Firm—Stevens, Davis, Miller & Mosher

[57] ABSTRACT

New 3-vinylcephalosporin derivatives of the general formula:

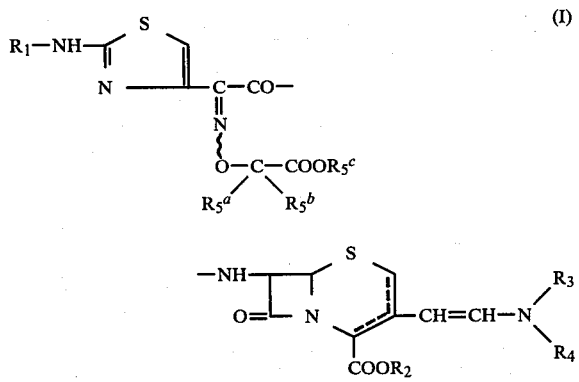

in the form of a bicyclooct-2-ene or bicyclooct-3-ene, in which formula $R_5{}^a$ and $R_5{}^b$ are hydrogen atoms or alkyl radicals, or together form an alkyl radical containing 2 or 3 carbon atoms, $R_5{}^c$ is an acid-protecting radical, $R_1$ is an amino-protecting radical, $R_2$ is an acid-protecting radical or a radical which can be removed by an enzymatic method, and $R_3$ and $R_4$, which are identical or different, represent alkyl (optionally substituted by hydroxyl, alkoxy, amino, alkylamino or dialkylamino) or phenyl, or together form, with the nitrogen atom, a saturated heterocyclic ring of 5 or 6 members, optionally containing another hetero-atom, their E and Z forms, and their syn and anti forms, and mixtures thereof, and also their preparation. These new compounds are useful as intermediates for the preparation of biologically active cephalosporins.

4 Claims, No Drawings

3-VINYLCEPHALOSPORIN DERIVATIVES

The present invention provides new 3-vinylcephalosporins of the general formula:

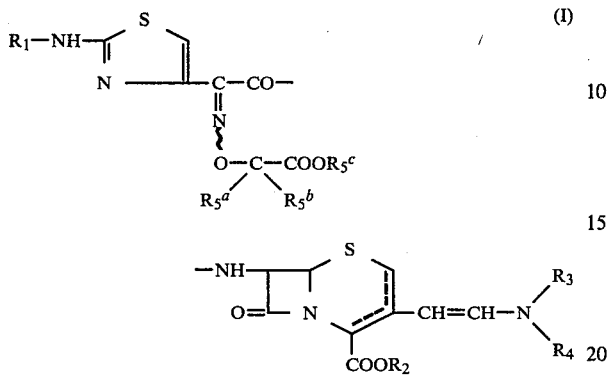

in the form of bicyclooct-2-enes or bicyclooct-3-enes in in which the substituent in the 3-position of the bicyclooctene is in the E or Z form or a mixture thereof and the imine group of the substituent in the 7-position is in the syn or anti form or a mixture thereof; wherein $R^a_5$ and $R^b_5$, which are identical or different, represent hydrogen atoms or alkyl radicals, or together form an alkylene radical containing 2 or 3 carbon atoms; $R^c_5$ represents an acid-protecting radical; $R_1$ represents an amine-protecting radical; $R_2$ represents a radical which can easily be removed by an enzymatic method and having the formula:

$$-\underset{\underset{R_6}{|}}{CH}-OCOR_7 \qquad (II)$$

in which $R_6$ represents a hydrogen atom or an alkyl radical and $R_7$ represents an alkyl radical or the cyclohexyl radical, or $R_2$ represents a methoxymethyl, t-butyl, benzhydryl, p-nitrobenzyl or p-methoxybenzyl radical; and the symbols $R_3$ and $R_4$, which are identical or different, represent alkyl radicals, which are unsubstituted or substituted by a hydroxyl, alkoxy, amino, alkylamino or dialkylamino radical or phenyl radicals, or together form, with the nitrogen atom to which they are attached, a saturated heterocyclic ring of 5 or 6 ring members, which may contain another hetero-atom chosen from nitrogen, oxygen and sulphur, and is unsubstituted or substituted by an alkyl radical, the above-mentioned alkyl portions or radicals being (unless otherwise mentioned) straight or branched and containing 1 to 4 carbon atoms.

3-Vinylcephalosporin derivatives are already known from French Patent Applications Nos. 2,081,451 and 2,137,899.

The compounds of formula (I) are distinguished by the fact that the vinyl group located in the 3-position itself carries an amino radical.

In the general formula (I), the compounds are in the form of bicyclooct-2-enes or bicyclooct-3-enes (according to the nomenclature of Chemical Abstracts), and the substituent on the carbon atom in the 3-position of the bicyclooctene exhibits cis/trans stereoisomerism. The symbol $R_1$ represents an amine-protecting radical, e.g. a t-butoxycarbonyl, 2,2,2-trichloroethoxycarbonyl, trityl, benzyl, dibenzyl, benzyloxycarbonyl, p-nitrobenzyloxycarbonyl, p-methoxybenzyloxycarbonyl, formyl, chloroacetyl, trichloroacetyl or trifluoroacetyl radical, and the symbol $R^c_5$ represents an acid-protecting radical, e.g. a methoxymethyl, t-butyl, benzhydryl, benzyl, nitrobenzyl or p-methoxybenzyl radical.

Furthermore, the acyloxyimino group of the substituent in the 7-position can be in either the syn position of formula (IIIa) or the anti position of the formula (IIIb):

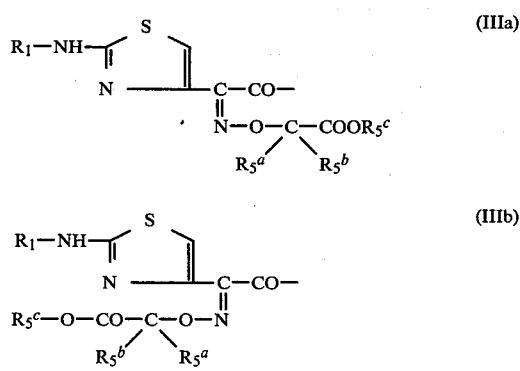

and these isomers, and mixtures thereof, fall within the scope of the invention.

Furthermore, if $R^a_5$ and $R^b_5$ are different, the invention relates to the corresponding diastereoisomers and also to mixtures thereof.

1. According to the invention, the products of the general formula (I) in which $R_3$ and $R_4$ are defined as above, except that they cannot represent alkyl substituted by hydroxyl, amino or alkylamino, can be obtained by reacting a compound, optionally prepared in situ, of the general formula:

[in which $R_3$ and $R_4$ are defined as above and $R_8$ and $R'_8$, which are identical or different, either represent groups of the general formula:

in which $X_2$ is an oxygen atom and $R_9$ represents an alkyl radical containing 1 to 5 carbon atoms or a phenyl radical, or represent in one case a radical of the general formula (V) in which $X_2$ is oxygen or sulphur, and in the other case an amino radical of the general formula:

in which $R_{10}$ and $R_{11}$ are defined in the same way as $R_3$ and $R_4$ in the general formula (IV), or also represent in each case a radical of the general formula (VI)] with a cephalosporin derivative of the general formula:

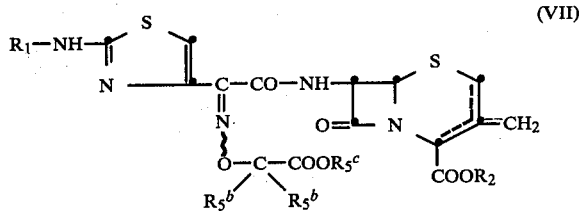

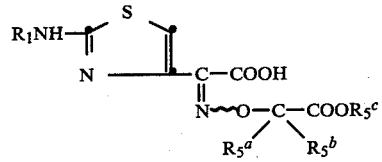

in which, the various symbols being defined as above, the derivative is in the form of a 3-methylbicyclooct-2-ene or 3-methylbicyclooct-3-ene or a 3-methylenebicyclooctane.

The reaction is generally carried out in an organic solvent such as dimethylformamide, hexamethylphosphorotriamide, acetonitrile, dimethylacetamide, ethyl acetate, dioxane, or a chlorinated solvent (e.g. 1,2-dichloroethane), or in a mixture of such solvents, at a temperature between 20° C. and the reflux temperature of the reaction mixture.

If a product of the general formula (IV) in which the radical (VI) is different from $-NR_3R_4$ is chosen, it is preferable to choose this product so that the amine $HNR_{10}R_{11}$ is more volatile than $HNR_3R_4$.

2. In a subsequent step, the products of the general formula (I) in which $R_3$ and $R_4$, which are identical or different, represent alkyl radicals substituted by hydroxyl, amino or alkylamino, and the other symbols are defined as above, can be obtained by trans-enamination from a product of the general formula (I) in which $R_3$ and $R_4$ represent alkyl radicals, preferably methyl radicals.

The reaction is carried out by reacting an amine of the general formula:

(VIII)

(in which $R_3$ and $R_4$ have the corresponding definitions) with the product of the general formula (I), under conditions analogous to those described above for reacting a product of the general formula (IV) with a derivative of the general formula (VII).

The products of the general formula (IV) can be prepared in accordance with the methods described by H. Bredereck et al., Chem. Ber. 101, 41 (1968), Chem. Ber. 101, 3,058 (1968) and Chem. Ber. 106, 3,725 (1973).

The cephalosporin derivatives of the general formula (VII) can be prepared from the products of the general formula:

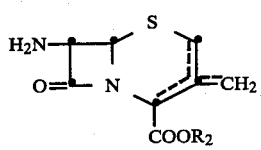

[in which, $R_2$ being defined as above, the position of the double bond is defined as for the product of the general formula (VII)] by reaction with an acid of the general formula:

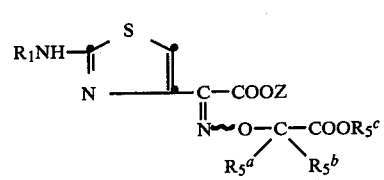

[in which the various symbols are defined as above] or a reactive derivative of this acid. It is understood that the acid of the general formula (X) in the syn or anti form, or mixtures thereof, leads respectively to the products of the general formula (VII) in the syn or anti form, or to mixtures thereof.

In general, the condensation of the products of the general formula (X), in which the acid group is free, with the 7-aminocephalosporin of the general formula (IX) is carried out in an organic solvent such as dimethylformamide, acetonitrile, tetrahydrofuran, methylene chloride or chloroform, in the presence of a condensation agent such as a carbodiimide (e.g. dicyclohexylcarbodiimide), N,N'-carbonyldiimidazole or 2-ethoxy-1-ethoxycarbonyl-1,2-dihydroquinoline, at a temperature between $-20°$ and $40°$ C.

If a reactive derivative of the acid of the general formula (X) is used, it is possible to use the anhydride, a mixed anhydride or a reactive ester of the general formula:

$$\begin{array}{c} R_1NH \underset{N}{\overset{S}{\bigsqcup}} \\ \phantom{R_1NH}\underset{N\sim O-C-COOR_5{}^c}{\overset{\phantom{S}}{\phantom{\bigsqcup}}}C-COOZ \\ \phantom{R_1NH\underset{N\sim O-C-}{}}R_5{}^a\phantom{x}R_5{}^b \end{array}$$

(XI)

[in which $R^a{}_5$, $R^b{}_5$, $R^c{}_5$ and $R_1$ are as defined above, and Z represents a succinimido, benzotriazol-1-yl, 4-nitrophenyl, 2,4-dinitrophenyl, pentachlorophenyl or phthalimido radical] or alternatively an acid halide, e.g. the acid chloride.

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of such solvents, [in the presence of an acid acceptor such as an epoxide (e.g. propylene oxide) or such as a nitrogen-containing organic base like pyridine, dimethylaminopyridine, N-methylmorpholine or a trialkylamine (e.g. triethylamine)], or in an aqueous-organic medium, in the presence of an alkaline condensation agent such as sodium bicarbonate, and the reaction is carried out at a temperature between $-40°$ and $+40°$ C.

If a reactive ester of the general formula (XI) is used, the reaction is generally carried out in the presence of a trialkylamine (e.g. triethylamine), in an organic solvent such as dimethylformamide, at a temperature between 0° and 40° C.

The products of the general formula (IX) can be prepared from a product of the general formula:

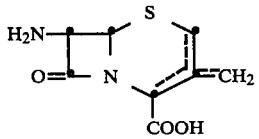 (XII)

[in which the position of the double bond is defined as for the product of the general formula (IX)] by applying the methods described in the literature:

if R₂ is methoxymethyl: according to S. SEKI et al., Tetrahedron Lett., 33, 2,915 (1977);

if R₂ is t-butyl: according to R. J. Stedman, J. Med. Chem., 9, 444, (1966);

if R₂ is benzhydryl: according to Dutch Patent Application No. 73/03,263; or if R₂ is benzyl, nitrobenzyl or p-methoxybenzyl: according to R. R. Chauvette et al., J. Org. Chem., 38 (17), 2,994 (1973).

The cephalosporin derivatives of the general formulae (VII) and (IX) in which R₂ represents a radical of the general formula (II) can be obtained by esterifying the corresponding acid by any method which is in itself known for preparing an ester from an acid without affecting the rest of the molecule.

In general, an alkali metal salt or a tertiary amine salt of a product of the general formula:

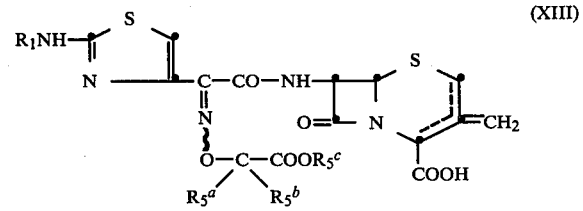 (XIII)

(in which the symbols are defined as above) or of the general formula (XII) [in which formulae the position of the double bond is defined as for the products of the general formula (VII)] is reacted with a halide of the general formula:

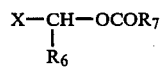 (XIV)

in which R₆ and R₇ are defined as above and X represents a halogen atom, in an inert solvent such as dimethylformamide, at a temperature between 0° and 30° C.

The compounds of the general formula (XIII) can be prepared from the products of the general formula (XII) by analogy with the preparation of the products of the general formula (VII) from the products of the general formula (IX).

The halides of the general formula (XIV) can be prepared in accordance with the method described in German Patent Application No. 23/50,230.

The products of the general formula (X) can be prepared by applying the method described in Belgian Pat. Nos. 864,810, 865,298, 876,541 and 876,542.

The new products of the general formula (I) are useful as intermediates for the preparation of 3-thio-vinyl-cephalosporins of the general formula:

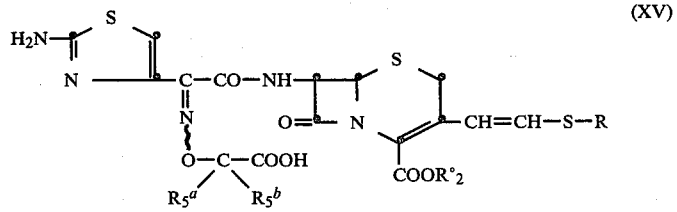 (XV)

in which the symbol R is chosen from amongst the following meanings:

(1) alkyl, L-2-amino-2-carboxyethyl or phenyl, (2) optionally N-oxidised pyrid-2-yl, pyrid-3-yl or pyrid-4-yl, (3) pyrimidin-2-yl, pyridazin-3-yl substituted in the 6-position (by an alkyl, methoxy, amino or acylamino radical) and optionally N-oxidised, or tetrazolo[4,5-b]pyridazin-6-yl, (4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, by (a) an alkyl radical containing 1 to 4 carbon atoms, which is unsubstituted or substituted by an alkoxy, alkylthio, phenyl, formyl, carbamoyl, alkylcarbamoyl, dialkylcarbamoyl, acyl, alkoxycarbonyl or thiazolidin-2-yl radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) an alkyl radical containing 2 or 4 carbon atoms, which is substituted by hydroxyl, carbamoyloxy, acyloxy (the acyl part of which can be substituted by an amino, alkylamino or dialkylamino radical), alkylsulphinyl, alkylsulphonyl, amino, alkylamino, dialkylamino, sulphoamino, alkylsulphonylamino, sulphamoylamino, acylamino (the acyl part of which is optionally substituted by hydroxyl, amino alkylamino or dialkylamino), alkoxycarbonylamino, ureido, alkylureido or dialkylureido, (d) a radical corresponding to one of the general formulae:

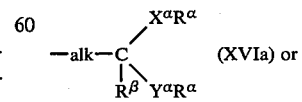 (XVIa) or

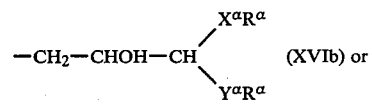 (XVIb) or

-continued

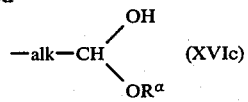

in which alk is an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) an alkyl radical containing 2 to 5 carbon atoms, which is substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl which is unsubstituted or substituted in the 3-position by alkoxycarbonyl, (7)

(a) 1,3,4-thiadiazol-5-yl which is unsubstituted or substituted by an alkyl, trifluoromethyl, alkoxy or akylthio radical, a hydroxyalkylthio radical, the alkyl part of which contains 2 to 4 carbon atoms, or an alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or (b) 1,2,4-thiadiazol-5-yl substituted by an alkyl or alkoxy radical, (8)

(a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or (b) oxazol-2-yl or 4-alkyloxazol-2-yl, (9) tetrazol-5-yl which is unsubstituted or substituted in the 1-position by (a) an alkyl radical containing 1 to 4 carbon atoms, which is unsubstituted or substituted by alkoxy, sulpho, carboxyl, formyl or sulphamoyl, (b) an alkyl radical containing 2 to 4 carbon atoms, which is substituted by hydroxyl, amino, alkylamino, dialkylamino, acylamino, carboxyalkylamino, sulphamoylamino, sulphoamino, ureido, alkylureido or dialkylureido, (c) an alkyl radical containing 2 to 5 carbon atoms, which is substituted by hydroxyimino or alkoxyimino, (d) a phenyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, or (e) a radical of the general formula (XVIa) in which $R^\beta$ represents a hydrogen atom, or a radical of the general formula (XVIb),

(10) 5,6-dioxo-1,4,5,6-tetrahydro-1,2,4-triazin-3-yl substituted in the 1-position, 5,6-dioxo-1,2,5,6-tetrahydro-1,2,4-triazin-3-yl substituted in the 2-position, or 1,2,4-triazol-5-yl or 3-alkoxycarbonyl-1,2,4-triazol-5-yl substituted in the 1-position, by (a) an alkyl radical which is itself substituted by an alkoxy, alkylthio, phenyl, formyl, carbamoyl, alkylcarbamoyl or dialkylcarbamoyl radical, a hydroxyalkylcarbamoyl radical (the alkyl part of which contains 2 to 4 carbon atoms) or an acyl, alkoxycarbonyl or thiazolidin-2-yl radical, or (b) a radical such as defined above under (4b), (c), (d) and (e),

(11) 5,6-dioxo-4-hydroxyalkylcarbamoylalkyl-1,4,5,6-tetrahydro-1,2,4-triazin-3-yl, the hydroxyalkyl part of which contains 2 to 4 carbon atoms, or

(12) 1-alkyl-5,6-dioxo-1,4,5,6-tetrahydro-1,2,4-triazin-3-yl substituted in the 4-position, 1-alkyl-5,6-dioxo-1,2,5,6-tetrahydro-1,2,4-triazin-3-yl substituted in the 2-position, 2-alkyl-5,6-dioxo-1,2,5,6-tetrahydro-1,2,4-triazin-3-yl substituted in the 1-position, or 4-alkyl-5,6-dioxo-1,4,5,6-tetrahydro-1,2,4-triazin-3-yl substituted in the 1-position, by a formylalkyl radical or by a radical of the general formula (XVIa) in which $R^\beta$ represents a hydrogen atom, and the symbol $R^o{}_2$ represents a hydrogen atom or a radical of the general formula (II).

The products of the general formula (XV) can be obtained from the products of the general formula (I) by the following procedure:

A product of the general formula:

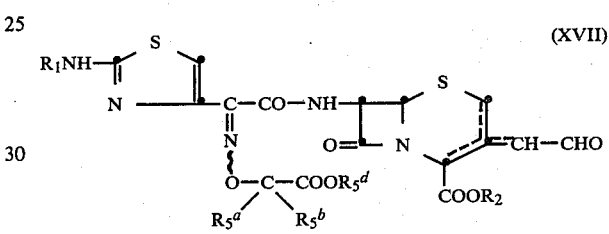

[in which $R^d{}_5$ is defined in the same way as $R^c{}_5$ or represents a hydrogen atom, and the other symbols are defined as above,] and which is in the form of a bicyclooct-2-ene or bicyclooct-3-ene or a 3-oxoethylidenebicyclooctane is prepared by hydrolysing the enamine of the general formula (I) according to the invention, or a mixture of its isomers, and then removing the protective radical $R^c{}_5$, if appropriate.

Preferably, an enamine of the general formula (I) in which $R_3$ and $R_4$ represent a methyl radical is hydrolysed.

The reaction is generally carried out in an organic acid (e.g. formic acid or acetic acid) or a mineral acid (e.g. hydrochloric acid or sulphuric acid), in the presence or absence of a solvent, in an aqueous or organic medium, at a temperature between $-20°$ C. and the reflux temperature of the reaction medium, and this is followed by treatment with an inorganic base (alkali metal bicarbonate) or an organic base (tertiary amine or pyridine).

If the reaction is carried out in an organic medium, the hydrolysis is performed by adding water to the reaction medium.

If the reaction is carried out in the presence of a solvent, it is not necessary for the solvent to be miscible with the acid aqueous phase. Contact is then effected by vigorous stirring.

Amongst the solvents which can be used, there may be mentioned chlorinated solvents, ethyl acetate, tetrahydrofuran, acetonitrile, dimethylformamide and alcohols.

It is not absolutely necessary to have purified the intermediate of the general formula (I) in order to carry out this reaction.

If it is desired to prepare a product of the general formula (XVII) in which $R^{d}_5$ represents a hydrogen atom, it is necessary to use an enamine of the general formula (I) in which the protective radicals of the acid groups ($R^{c}_5$ and $R_2$) are different and can be removed selectively.

The removal of the protective radical $R^{c}_5$ is carried out under conditions which will be described below.

The product of the general formula (XVII) can be oxidised to the product of the general formula:

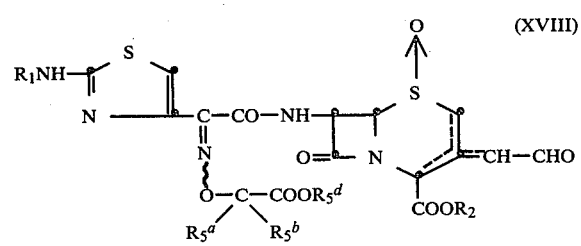

(in which the symbols have the corresponding definition, and which is in the form of a bicyclooct-2-ene or 3-oxoethylidenebicyclooctane) by applying the method described in German Patent Application No. 26/37,176.

A product of the general formula:

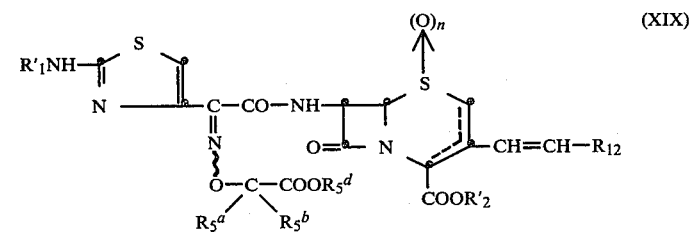

[in which $R'_1$ represents hydrogen or a radical $R_1$ as defined above; $R'_2$ represents hydrogen or a radical $R_2$ as defined above; $R^{a}_5$, $R^{b}_5$ and $R^{d}_5$ are defined as above (it being understood that if n=0, the product is in the form of a bicyclooct-2-ene or bicyclooct-3-ene, and if n=1, the product is in the form of a bicyclooct-2-ene); the substituent on the carbon atom in the 3-position of the bicyclooctene exhibits E/Z stereoisomerism, and the symbol $R_{12}$ represents a radical of the general formula:

$$R'_{12}-SO_2O-(XX) \text{ or } R''_{12}-COO- \quad (XXI)$$

(in which formulae $R'_{12}$ represents an alkyl, trifluoromethyl or trichloromethyl radical or a phenyl radical which is unsubstituted or substituted by a halogen atom or by an alkyl or nitro radical and $R''_{12}$ is defined in the same way as $R_{12}$ or represents an acylmethyl, 2-acylethyl, 2-acylpropyl, alkoxycarbonylmethyl, 2-alkoxycarbonylethyl or 2-alkoxycarbonylpropyl radical) or a halogen atom chosen from amongst chlorine, bromine and iodine] is prepared by reacting an activated form of an acid $R'_{12}-SO_3H$ or $R''_{12}-COOH$, of the formulae:

$(R'_{12}SO_2)_2O$      (XXII)

$R'_{12}SO_2Hal$      (XXIII)

$(R''_{12}CO)_2O$      (XXIV)

$R''_{12}COHal$      (XXV)

(Hal representing a halogen atom) or by reacting a halogenating reagent, with a product of the general formula (XVII) or (XVIII) or with a mixture of its isomers, this being followed, if appropriate, by the reduction of the sulphoxide obtained and, if necessary, by the removal of the protective groups of the amine groups ($R_1$) and/or, if appropriate, of the acid groups ($R_2$ and/or $R^{d}_5$), if it is desired to obtain a product of the general formula (XIX) in which the amine and/or acid groups are free.

The reaction is generally carried out in the presence of a tertiary base of the general formula:

in which $X_1$, $Y_1$ and $Z_1$ represent alkyl or phenyl radicals or, if appropriate, two of them form a ring with the nitrogen atom to which they are attached (e.g. in the presence of triethylamine or N,N-dimethylaniline), in a chlorinated organic solvent (e.g. methylene chloride), in an ester (e.g. ethyl acetate), in an ether (e.g. dioxane or tetrahydrofuran), in an amide (e.g. dimethylacetamide or dimethylformamide), in acetonitrile or N-methylpyrrolidone or in a mixture of such solvents, or directly in a basic solvent such as pyridine, or alternatively, if $R_{12}$ is other than a halogen atom, the reaction can be carried out in an aqueous-organic medium, in the presence of an alkaline condensation agent (e.g. an alkali metal bicarbonate, sodium hydroxide or potassium hydroxide), at a temperature between $-78°$ C. and the reflux temperature of the reaction mixture.

If appropriate, the reaction is carried out under nitrogen.

It is not absolutely necessary to have purified the intermediate of the general formulae (XVII) or (XVIII) in order to carry out this reaction.

If it is desired to prepare a product of the general formula (XIX) in which $R_{12}$ is a halogen atom, the reaction is carried out starting from a product of the general formula (XVII) or (XVIII) in which $R^{d}_5$ is a protective radical $R^{c}_5$. The halogenating agents can be chosen from amongst halogen derivatives of phosphorus, in particular:

halogen addition compounds of triarylphosphite, or phosphorus trichloride, phosphorus oxychloride, phosphorus pentachloride, dichlorotriphenylphosphorane or catechyltrichlorophosphorane if $R_{12}$ is a chlorine atom, or phosphorus tribromide, phosphorus oxybromide, phosphorus pentabromide or catechyltribromophosphorane if $R_{12}$ is a bromine atom.

If phosphorus trichloride (or tribromide) is used, this reagent is reacted with a product of the general formula (XVII).

Catechyltrichlorophosphorane (or catechyltribromophosphorane), which can be prepared in situ, can be obtained in accordance with the method described by H. Gross and U. Karsch, J. Prakt. Chem., 29, 315 (1965).

The halogen addition compounds of triarylphosphite, which can be formed in situ, are described by H. N. Rydon and B. L. Tonge, J. Chem. Soc., 3,043 (1956), by J. Michalski et al., J. Org. Chem., 45, 3,122 (1980), or in Belgian Pat. No. 881,424, and can be prepared in accordance with the methods mentioned in these documents.

The preparation of the halogen derivatives of the general formula (XIX) is carried out in an anhydrous medium.

If it is desired to prepare a product of the general formula (XIX) in which $R_{12}$ is a chlorine or bromine atom, depending on the operating conditions, it is possible to isolate the dihalogen intermediate of the general formula:

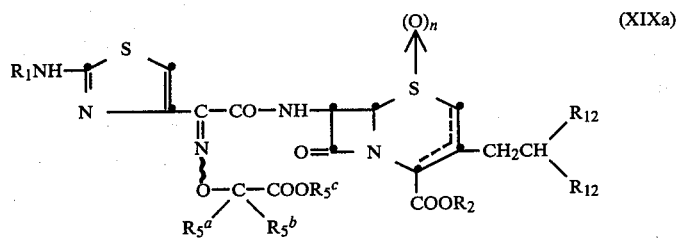

(XIXa)

[in which $R_1$, $R_2$, $R^a_5$, $R^b_5$ and $R^c_5$ are defined as in the general formula (XVII) and $R_{12}$ is defined as above, and which is in the form of a bicyclooct-2-ene (or bicyclooct-3-ene) if $n=0$, or in the form of a bicyclooct-2-ene if $n=1$], which is then dehydrohalogenated.

If it is desired to isolate the dihalogen intermediate, the reaction is carried out with a halogenating agent, in an organic solvent such as a chlorinated solvent (e.g. methylene chloride, chloroform, carbon tetrachloride or 1,2-dichloroethane), an ether (e.g. ethyl ether, propylene oxide, tetrahydrofuran or dioxane), an amide (e.g. dimethylacetamide, dimethylpropionamide, dimethylformamide, N-acetylmorpholine, N-acetylpiperidine or N-methylpyrrolidone) or a mixture of such solvents, at a temperature which is slightly lower than for the preparation of the corresponding halogenovinyl derivative, i.e. between $-78°$ and $30°$ C. It is also possible to carry out the reaction in the presence of a base such as pyridine, in one of the above solvents, at a temperature between $-78°$ and $0°$ C.

The dehydrohalogenation is carried out in the presence of a tertiary base as defined above, an aromatic amine (e.g. pyridine, picoline or quinoline) or an inorganic base (such as sodium hydroxide, potassium hydroxide, or alkali metal carbonate or bicarbonate or an alkaline earth metal carbonate), in an organic or aqueous-organic medium, in the above-mentioned solvents, at a temperature between $-20°$ C. and the reflux temperature of the reaction mixture.

It is not absolutely necessary to have purified the dihalogen intermediate in order to carry out the dehydrohalogenation thereof.

The redution of the S-oxide can be carried out under the conditions described in German Patent Application 2,637,176.

If necessary, the removal of the protective radicals of the amine group ($R_1$) and of the acid groups ($R^c_5$ and/or $R_2$) can be carried out simultaneously or successively. By way of example:

1. The removal of the amine-protecting groups is carried out:

in the case of a t-butoxycarbonyl, trityl, p-methoxybenzyloxycarbonyl or formyl radical: by treatment in an acid medium. Preferably, trifluoroacetic acid is used, the reaction being carried out at a temperature between $0°$ and $20°$ C., or alternatively orthophosphoric or polyphosphoric acids are used pure or in the presence of water at a temperature between $20°$ and $60°$ C., or para-toluenesulphonic or methanesulphonic acid is used, in acetone, at the reflux temperature of the reaction mixture. Under these conditions, the product of the general formula (XIX) can be obtained in the form of the trifluoroacetate, the solvate with formic acid, the phosphate, the methanesulphonate or the para-toluenesulphonate, from which the amine group can be freed by any method which is in itself known for obtaining an amine from one of its salts without affecting the rest of the molecule. The reaction is carried out, in particular, by bringing the compound into contact with an ion exchange resin or by reaction with an organic base.

in the case of a 2,2,2-trichloroethoxycarbonyl or p-nitrobenzyloxycarbonyl radical: by reduction (in particular treatment with zinc in acetic acid).

in the case of a chloroacetyl or trichloroacetyl radical: by applying the method described in the French Patent published under No. 2,243,199.

in the case of a benzyl, dibenzyl or benzyloxycarbonyl radical: by catalytic hydrogenation.

in the case of a trifluoroacetyl radical: by treatment in a basic medium.

2. The removal of the protective groups of the carboxyl radical is carried out:

in the case of a t-butyl, p-methoxybenzyl or benzhydryl group: by treatment in an acid medium, under the conditions described above for the removal of the amino-protecting trityl radical. In the case of the benzhydryl radical, the reaction can be carried out in the presence of anisole.

in the case of a methoxymethyl group: by treatment in a dilute acid medium.

in the case of a nitrobenzyl group: by reduction (in particular treatment with zinc in acetic acid or hydrogenolysis).

I. The 3-thiovinylcephalosporins of the general formula (XV) in which R does not contain a substituent of the general formula (XVIc) can be prepared by reacting a thiol (or one of its alkali metal or alkaline earth metal salts) of the general formula:

R—SH (XXVII)

in which R, which is defined as above, except that it cannot contain a substituent of the general formula (XVIc), is optionally protected, with a cephalosporin derivative (or a mixture of the isomers) of the general formula (XIX), in which the symbols are defined as above, this being followed by the reduction of the sulphoxide obtained (if n=1) and then, if appropriate, by the removal of the protective radicals.

If it is desired to obtain a product of the general formula (XV) in which R contains a formyl or acylalkyl radical, a thiol of the general formula (XXVII) in which this radical is protected in the form of an acetal [as defined by the general formulae (XVIa) and (XVIb)] is used.

It is understood that, if the radical R of the product of the general formula (XXVII) contains a group capable of interfering with the reaction, it is preferable to protect this group by any method which is in itself known and which does not affect the rest of the molecule.

In the case of an amino or alkylamino group, the protection is effected by a radical such as $R_1$ defined above.

In the case of a carboxyl group, the protection is effected by a radical such as methoxymethyl, t-butyl, benzhydryl, p-nitrobenzyl or p-methoxybenzyl.

In the case of hydroxyl groups, the protection is effected by a radical such as trityl, tetrahydropyranyl or 2-methoxyprop-2-yl, or alternatively, in the case of the 2,3-dihydroxypropyl or 1,3-dihydroxyprop-2-yl groups, as a cyclic acetal in the form of 2,2-dimethyldioxolan-4-yl-methyl or 2,2-dimethyldioxan-5-yl radicals.

Furthermore, it is understood that, if the radical R of the product of the general formula (XXVII) contains a hydroxyl, sulpho, sulphinyl or sulphonyl radical, it is preferable to use a product of the general formula (XIX) in which n=0.

The reaction of the products of the general formulae (XXVII) and (XIX) is generally carried out in the presence of a base such as a pyridine or a tertiary organic base of the general formula (XXVI). The base used is e.g. diisopropylethylamine or diethylphenylamine.

If a salt of the thiol of the general formula (XXVII) is used, it is not necessary to carry out the reaction in the presence of an organic base as defined above.

The reaction is advantageously carried out in an organic solvent such as dimethylformamide, tetrahydrofuran, methanol, ethanol or acetonitrile, or a mixture of such solvents.

It is also possible to carry out the reaction in the presence of an alkali metal bicarbonate, in a solvent such as mentioned above, if appropriate in the presence of water. The reaction is carried out at a temperature between −20° C. and the reflux temperature of the reaction mixture, the chosen temperature varying according to the thiol employed. Likewise, the reaction time can vary from 5 minutes to 48 hours, according to the thiol employed.

If appropriate, the reaction is carried out under nitrogen.

Preferably, if it is desired to use a bicyclooct-3-ene of the general formula (XIX), a product of this type in which $R'_2$ is other than hydrogen and $R^{d}_5$ is defined as above is used.

The reduction of the oxide and the removal of the amine-protecting or acid-protecting groups are carried out in accordance with the methods described above.

The removal of the protective radicals of hydroxyl groups is carried out:

by acidolysis, e.g. with trifluoroacetic acid, aqueous or non-aqueous formic acid or para-toluenesulphonic acid in the case of the trityl, tetrahydropyranyl, 2,2-dimethyldioxolan-4-yl-methyl or 2,2-dimethyldioxan-5-yl radical [if aqueous or non-aqueous formic acid is used, the freeing of the protected hydroxyl radicals can lead at least partially to the corresponding formic acid esters, which can be separated off by chromatography, if necessary], or in accordance with the method described in Belgian Pat. No. 875,379 in the case of the 2-methoxyprop-2-yl radical.

The removal of the protective radicals in the groups of the general formula (XVIa) or (XVIb) (if it is desired to obtain a product of the general formula (XV) in which R contains a formyl or acylalkyl radical) is carried out:

in the presence of a sulphonic acid (e.g. methanesulphonic acid or p-toluenesulphonic acid), in an organic solvent (e.g. acetonitrile or acetone), if appropriate in the presence of water and if appropriate in the presence of a reagent which can be converted to an acetal, such as acetone, glyoxylic acid, benzaldehyde or pyruvic acid, at a temperature between 20° C. and the reflux temperature of the reaction mixture, or alternatively, if the radical R is a 5,6-dioxo-1,4,5,6-tetrahydro-1,2,4-triazin-3-yl radical, by reaction with pure or aqueous formic acid (preferably containing less than 10% of water), either in the presence of absence of silica, or by trans-acetalisation in the presence of a reagent which can be converted to an acetal, as defined above.

The thiols of the general formula (XXVII) (which can be used in their tautomeric form) can be prepared by applying one of the following methods, depending on the meaning of the radical R:

if R is a pyrid-3-yl radical: in accordance with the method described by H. M. Wuest and E. H. Sakal, J. Amer. Chem. Soc., 73, 1,210 (1951), if R is a pyrid-3-yl-1-oxide radical: in accordance with the method described by B. Blank et al., J. Med. Chem. 17, 1,065 (1974), if R is a pyrid-4-yl-1-oxide radical: in accordance with the method described by R. A. Y. Jones et al., J. Chem. Soc. 2,937 (1960), if R is a pyridazin-3-yl radical substituted by alkyl or methoxy and optionally N-oxidised: in accordance with the method described in Belgian Pat. No. 787,635, if R is a pyridazin-3-yl radical substituted by amino and optionally N-oxidised: in accordance with the method described in Belgian Pat. No. 579,291, if R is a pyridazin-3-yl radical substituted by acylamino and optionally N-oxidised: by applying the methods described by M. Kumagai and M. Bando, Nippon Kagaku Zasshi, 84, 995 (1963), and by T. Horie and T. Ueda, Chem. Pharm. Bull., 11, 114 (1963), if R is a tetrazolo[4,5-b]pyridazin-6-yl radical: in accordance with the method described in Belgian Pat. No. 804,251, if R is a 5,6-dioxo-1,4,5,6-tetrahydro-1,2,4-triazin-3-yl radical substituted in the 4-position, or a 2-alkoxycarbonyl-1,3,4-triazol-5-yl radical substituted in the 1-position, by a radical R$^\gamma$ chosen from amongst:

(a) an allyl radical, an alkyl radical (containing 1 to 4 carbon atoms, which is itself optionally substituted by an alkoxy, alkylthio, phenyl, carbamoyl, alkylcarbamoyl, dialkylcarbamoyl, acyl, alkoxycarbonyl or thiazolidin-2-yl radical), (b) a 2,3-dihydroxypropyl or 1,3-dihydroxyprop-2-yl radical (optionally protected in the form of a cyclic acetal), (c) an alkyl radical [containing 2 to 4 carbon atoms, which is itself substituted by hydroxyl, carbamoyloxy, dialkylamino, alkylsulphinyl, alkylsulphonyl, alkylsulphonylamino, sulphamoylamino, acylamino (optionally substituted), alkoxycarbonylamino, ureido, alkylureido or dialkylureido], (d) a radical of the general formula (XVIa) or (XVIb), or (e) a hydroxyiminoalkyl or alkoxyiminoalkyl radical, or if R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl radical substituted in the 1-position, by a radical R$^\gamma$ as defined above (except that it cannot represent an unsubstituted alkyl radical) or by a hydroxyalkylcarbamoylalkyl radical, the hydroxyalkyl portion of which contains 2 to 4 carbon atoms, or if R is a 5,6-dioxo-4-hydroxyalkylcarbamoylalkyl-1,4,5,6-tetrahydro-1,2,4-triazin-3-yl radical, the hydroxyalkyl portion of which contains 2 to 4 carbon atoms: by reacting an alkyl oxalate or an alkyl monooxalate halide with a thiosemicarbazide of the general formulae:

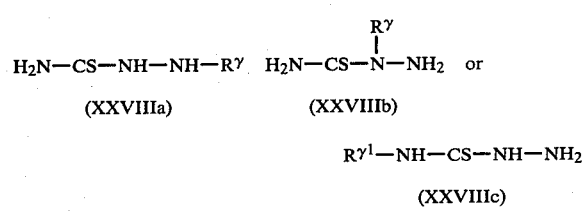

(in which R$^\gamma$ is defined as above and R$^{\gamma1}$ represents a hydroxyalkylcarbamoylalkyl radical or the radical R$^\gamma$). The reaction is carried out in the presence of an alkali metal alcoholate, e.g. sodium ethylate or methylate or potassium t-butylate, by applying the method described by M. Pesson and M. Antoine, Bull. Soc. Chim. France 1,590 (1970).

It is not absolutely necessary to purify the product obtained (or to free the protected radicals) in order to use it for the preparation of the products of the general formula (XV).

The thiosemicarbazides of the general formulae (XXVIIIa) to (XXVIIIc) can be prepared in accordance with one of the methods described by K. A. Jensen et al., Acta Chem. Scand., 22, 1 (1968), or by applying the method described by Y. Kazakov and J. Y. Potovskii, Doklady Acad. Nauk. SSSR 134, 824 (1960), it being understood that, if R$^\gamma$ contains an amino radical, the latter is protected.

The protection of the amino radical and the removal of the protective radical are carried out in accordance with the usual methods which do not affect the rest of the molecule. The t-butoxycarbonyl group, which can be removed by acid hydrolysis, is used in particular.

If R is a 1,3,4-triazol-5-yl radical substituted in the 1-position by:

an alkyl, allyl or alkoxyalkyl radical, an alkyl radical (1 to 4 carbon atoms) which is itself substituted as defined above under (a), except that it cannot be substituted by a thiazolidin-2-yl radical, a radical as defined above under (c), or an alkoxyiminoalkyl radical: by applying one of the methods described by M. Pesson and M. Antoine, Bull. Soc. Chim. France 1,590 (1970).

If R is a 1,3,4-triazol-5-yl radical substituted in the 1-position by thiazolidin-2-yl-alkyl or hydroxyiminoalkyl: by reacting respectively cysteamine or hydroxylamine with a 1-dialkoxyalkyl-5-mercapto-1,3,4-triazole which can be obtained, by applying the method described by M. Kanaoka, J. Pharm. Soc. Japan, 75, 1,149 (1955), from a 4-dialkoxyalkylthiosemicarbazide.

If R is a 1,3,4-triazol-5-yl radical substituted in the 1-position by 2,3-dihydroxypropyl or 1,3-dihydroxyprop-2-yl (which are optionally protected in the form of a cyclic acetal), or represents a radical of the general formula (XVIa) or (XVIb): by applying the method described by M. Kanaoka, J. Pharm. Soc. Japan, 75, 1,149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by acyloxyalkyl (optionally substituted): by respectively acylating 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, the mercapto radical of which has been protected beforehand [e.g. according to C. G. Kruse et al., Tet. Lett. 1,725 (1976)], by any method known for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by sulphoaminoalkyl: from the corresponding product substituted by a t-butoxycarbonylaminoalkyl radical, by analogy with the method described in Belgian Pat. No. 847,237.

If R is a 1,4-dialkyl-5,6-dioxo-1,4,5,6-tetrahydro-1,2,4-triazin-3-yl or 1-alkyl-5,6-dioxo-1,4,5,6-tetrahydro-1,2,4-triazin-3-yl radical: in accordance with the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: in accordance with the method described by M. Pesson and M. Antoine, C.R. Acad. Sci., Ser C, 267, 25, 1,726 (1968).

If R is a 1,2,3-triazol-5-yl radical: in accordance with the method described in French Patent Application No. 2,215,942.

If R is a 1,3,4-triazol-5-yl radical: in accordance with the method described by M. Kanaoka, J. Pharm. Soc. Jap. 75, 1,149 (1955).

If R is a 1,3,4-thiadiazol-5-yl radical optionally substituted by alkyl, alkoxy, alkylthio, alkylsulphonyl, amino, alkylamino, dialkylamino or acylamino: in accordance with the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: in accordance with the method described in German Patent Application No. 2,446,254.

If R is a 1,3,4-thiadiazol-5-yl radical substituted by a carboxyalkyl radical: by applying the method described in German Patent Application No. 1,953,861.

If R is a 1,3,4-thiadiazol-5-yl radical substituted by a trifluoromethyl radical: in accordance with the method described in German Patent Application No. 2,162,575.

If R is a 1,3,4-thiadiazol-5-yl radical substituted by a carboxyl radical: in accordance with the method described in Japanese Patent Application No. 77/48,666.

If R is a 1,3,4-thiadiazol-5-yl radical substituted by an acylaminoalkyl radical: in accordance with the method described in Japanese Patent Application No. 76/80,857.

If R is a 1,3,4-thiadiazol-5-yl radical substituted by a hydroxyalkylthio radical: by applying the method described by G. Nannini, Arz. Forsch. 27 (2), 343 (1977).

If R is a 1,2,4-thiadiazol-5-yl radical substituted by alkyl or alkoxy: in accordance with the method described in German Patent Application No. 2,806,226 or according to Chem. Ber. 90, 184 (1957).

If R is a 1,3,4-oxadiazol-5-yl radical as defined above under 8(a): by applying the method described by E. Hoggarth, J. Chem. Soc. 4,811 (1952).

If R is an oxazol-2-yl or 4-alkyloxazol-2-yl radical: by applying the method previously described by C. Bradsher, J. Org. Chem. 32, 2,079 (1967).

If R is a tetrazol-5-yl radical optionally substituted in the 1-position by alkyl, hydroxyalkyl or phenyl: in accordance with the methods described in Belgian Pat. No. 830,821.

If R is a tetrazol-5-yl radical substituted in the 1-position by alkoxyalkyl: by adding sodium azide to an isothiocyanatoalkoxyalkyl compound, the reaction being carried out in an organic solvent such as ethanol, at the reflux temperature of the reaction mixture.

The isothiocyanatoalkoxyalkyl compound can be obtained by applying the method described by E. Schmidt et al., Chem. Ber. 73, 286 (1940).

If R is a tetrazol-5-yl radical substituted in the 1-position by a carboxyalkyl radical: in accordance with the method described in Belgian Pat. No. 858,112.

If R is a tetrazol-5-yl radical substituted in the 1-position by a sulphoalkyl radical: in accordance with the method described in Belgian Pat. No. 856,498 or described by D. A. Berges et al., J. Het. Chem. 15, 981 (1978).

If R is a tetrazol-5-yl radical substituted in the 1-position by an aminoalkyl, alkylaminoalkyl or dialkylaminoalkyl radical: by applying the method described in German Patent Application No. 2,738,711.

If R is a tetrazol-5-yl radical substituted in the 1-position by a sulphamoylalkyl, sulphamoylaminoalkyl or sulphoaminoalkyl radical: in accordance with the method described in Belgian Pat. No. 856,636.

If R is a tetrazol-5-yl radical substituted by an acylaminoalkyl radical, or a 1,3,4-thiadiazol-5-yl radical substituted by hydroxyl: in accordance with the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (the mercapto radical of which has been protected beforehand), by treatment with an alkali metal isocyanate, with an alkyl isocyanate or with a dialkylcarbamoyl halide, and then freeing of the mercapto group under the conditions described in Belgian Pat. No. 847,237.

If R is a tetrazol-5-yl radical substituted in the 1-position by a carboxyalkylaminoalkyl radical: in accordance with the method described in German Patent Application No. 2,715,597.

If R is a tetrazol-5-yl radical substituted in the 1-position by a 2,3-dihydroxypropyl radical: in accordance with the method described in U.S. Pat. No. 4,064,242.

If R is a tetrazol-5-yl radical substituted in the 1-position by a 1,3-dihydroxyprop-2-yl radical: by adding sodium azide to a 2,2-dimethyl-1,3-dioxolan-5-yl isothiocyanate (and then freeing the hydroxyl groups, if appropriate).

If R is a tetrazol-5-yl radical substituted in the 1-position by a radical of the general formula (XVIa) or (XVIb) as defined as above under 9(e), or a radical defined above under 9(c): by reacting sodium azide with the corresponding isothiocyanate, by analogy with the method described by R. E. Orth, J. Pharm. Sci. 52 (9), 909 (1963), it being understood that, in the case where R contains a hydroxyl or hydroxyiminoalkyl substituent, the alcohol or the oxime are optionally protected, e.g. by a tetrahydropyranyl group.

If R is a 1,2,4-triazol-5-yl radical substituted in the 1-position by:

an allyl or alkoxyalkyl radical, an alkyl radical (1 to 4 carbon atoms) which is itself substituted as defined above under 10(a), except that it cannot be substituted by a thiazolidin-2-yl radical, a hydroxyalkylcarbamoylalkyl radical, the hydroxyalkyl part of which contains 2 to 4 carbon atoms, a radical as defined above under 4(c), or an alkoxyiminoalkyl radical: by analogy with the methods described by M. Pesson and M. Antoine, Bull. Soc. Chim. France, 1,599 (1970), or C.R. Acad. Sci., Ser C, 267, (25), 1,726 (1968).

If R is a 1,2,4-triazol-5-yl radical substituted in the 1-position by thiazolidin-2-yl-alkyl or by hydroxyiminoalkyl: by reacting respectively cysteamine or hydroxylamine with a 1-dialkoxyalkyl-5-mercapto-1,2,4-triazole which can be obtained, by analogy with the method described by M. Kanaoka, J. Pharm. Soc. Japan, 75, 1,149 (1955), from a 4-dialkoxyalkylthiosemicarbazide.

If R is a 1,2,4-triazol-5-yl radical substituted in the 1-position by 2,3-dihydroxypropyl or 1,3-dihydroxyprop-2-yl (which are optionally protected in the form of a cyclic acetal) or by a radical of the general formula (XVIa) or (XVIb): by analogy with the method described by M. Kanaoka, J. Pharm. Soc. Japan, 75, 1,149 (1955).

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by acyloxyalkyl (optionally substituted): by respectively acylating 5,6-dioxo-1-hydroxyalkyl-3-mercapto-1,4,5,6-tetrahydro-1,2,4-triazine, 5,6-dioxo-2-hydroxyalkyl-3-mercapto-1,2,5,6-tetrahydro-1,2,4-triazine, 3-alkoxycarbonyl-1-hydroxyalkyl-5-mercapto-1,2,4-triazole or 1-hydroxyalkyl-5-mercapto-1,2,4-triazole, the mercapto radical of which has been protected beforehand [e.g. according to C. G. Kruse et al., Tet. Lett. 1,725 (1976)], by any method known for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by sulphoaminoalkyl: from the corresponding product substituted by a t-butoxycarbonylaminoalkyl radical, by analogy with the method described in Belgian Pat. No. 847,237.

If R is a 1-alkyl-5,6-dioxo-1,4,5,6-tetrahydro-1,2,4-triazin-3-yl radical substituted in the 4-position, a 1-alkyl-5,6-dioxo-1,2,5,6-tetrahydro-1,2,4-triazin-3-yl radical substituted in the 2-position, a 2-alkyl-5,6-dioxo-1,2,5,6-tetrahydro-1,2,4-triazin-3-yl radical substituted in the 1-position, or a 4-alkyl-5,6-dioxo-1,4,5,6-tetrahydro-1,2,4-triazin-3-yl radical substituted in the 1-position, by a formylalkyl radical or by a radical of the general formula (XVIa) in which $R^\beta$ represents a hydrogen atom: by reacting an alkyl oxalate with a thiosemicarbazide, by analogy with the method described by M. Pesson and M. Antoine, C.R. Acad, Sci. 267 (15C), 904 (1968), or C.R. Acad. Sci. 267 (25C), 1,726 (1968). II. The thiovinylcephalosporins of the general formula (XV) in which R does not contain a substituent of the general formula (XVIc) can also be prepared by reacting a thiol of the general formula (XXVII) (or one of its alkali metal or alkaline earth metal salts), in which R, which is defined as above, is optionally protected, with a cephalosporin derivative (or a mixture of the isomers) of the general formula (XIXa), then reducing the sulphoxide obtained (if n=1) and then removing the protective radicals. The protection of the radical R of the product of the general formula (XXVII) is the same as defined above for the preparation of a product of the general formula (XV) from a product of the general formula (XIX) and a thiol of the general formula (XXVII).

The reaction is carried out under the conditions described above for the reaction of the products of the general formulae (XXVII) and (XIX).

If necessary, the reduction of the S-oxide and the removal of the protective groups are carried out in accordance with the methods described above. III. The thiovinylcephalosporins of the general formula (XV) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an alkyl radical containing 2 to 4 carbon atoms, which is substituted by a carbamoyloxy group or acyloxy group (the acyl part of which is optionally substituted by an amino, alkylamino or dialkylamino radical), which are functional derivatives of the product of the general formula (XV) in which R is a radical — ⓡ —alk′—OH chosen from amongst 5,6-dioxo-1-(or 4-)hydroxyalkyl-1,4,5,6-tetrahydro-1,2,4-triazin-3-yl, 5,6-dioxo-2-hydroxyalkyl-1,2,5,6-tetrahydro-1,2,4-triazin-3-yl, 1-hydroxyalkyl-1,3,4-(or 1,2,4-)triazol-5-yl and 3-alkoxycarbonyl-1-hydroxyalkyl-1,2,4-triazol-5-yl, can be obtained by the carbamation or esterification of an alcohol of the general formula:

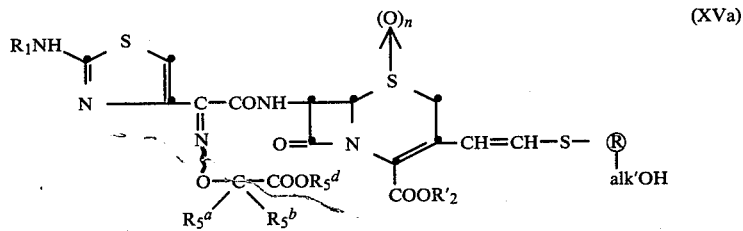

[in which $R'_2$, $R^a{}_5$, $R^b{}_5$, $R^d{}_5$, $R_1$ and n are defined as above and — ⓡ —alk′—OH is defined as above] by any method known for obtaining an ester or a carbamate from an alcohol without affecting the rest of the molecule, this being followed, if necessary, by the reduction of the sulphoxide obtained and the removal of the protective radicals.

The esterification is carried out at a temperature between $-50°$ C. and the reflux temperature of the reaction mixture, in particular by condensation of the acid anhydride (or of another reactive derivative, e.g. a halide), in an inert organic solvent such as an ether (e.g. tetrahydrofuran), a chlorinated solvent (e.g. methylene chloride) or a mixture of such solvents, in the presence of a nitrogen-containing base such as pyridine, 4-dimethylaminopyridine or a trialkylamine (triethylamine), or of an alkaline condensation agent (e.g. sodium bicarbonate), this being followed, if necessary by the reduction of the S-oxide obtained and the removal of the protective groups, in accordance with the methods described above.

If the acyloxy group substituted by amino contains only one carbon atom (carbamoyloxy group), the reaction is carried out in particular with chlorosulphonyl or trichloroacetyl isocyanate, in an inert organic solvent, e.g. tetrahydrofuran or acetonitrile, at a temperature between $-80°$ and 20° C., this being followed by the removal of the protective groups.

IV. The thiovinylcephalosporins of the general formula (XV) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an alkyl radical containing 2 to 4 carbon atoms, which is substituted by a sulphoamino, alkylsulphonylamino or sulphamoylamino group, an acylamino group (the acyl part of which is optionally substituted by hydroxyl, amino, alkylamino or dialkylamino), or an alkoxycarbonylamino, ureido, alkylureido or dialkylureido group, or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1-position by an alkyl radical containing 2 to 4 carbon atoms, which is substituted by an acylamino, sulphamoylamino, sulphoamino, ureido, alkylureido or dialkylureido group, and $R^o{}_1$ and $R^o{}_2$ have the corresponding definitions, which are all functional derivatives of the amine which corresponds thereto, can be obtained by treating an amine of the general formula:

carried out with respectively the corresponding chlorosulphonyl derivative, acid chloride, chloroformate or dialkylcarbamoyl chloride, under the conditions described above for the reaction of the acid chloride of the general formula (X) with the 7-aminocephalosporin of the general formula (IX).

If it is desired to prepare a product of the general formula (XV) in which the radical R contains a sulphoamino, alkylsulphonylamino or acylamino (substituted or unsubstituted) substituent, the reaction can be carried out by means of the corresponding acid anhydride, under the conditions described above for reacting the product of the general formula (X) in the form of the anhydride.

If it is desired to obtain a product of the general formula (XV) in which R contains an acylamino radical (substituted or unsubstituted), it is also possible to carry

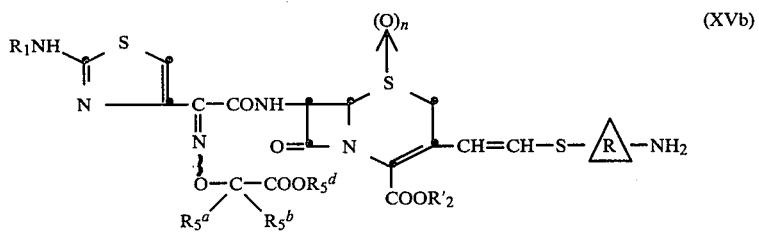

(XVb)

[in which $R^a{}_5$, $R^b{}_5$, $R^d{}_5$, $R_1$, $R'_2$ and n are defined as above for the product of the general formula (XVa), and —⟨R⟩—NH₂ represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an aminoalkyl radical, the alkyl part of which contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical, the alkyl part of which contains 2 to 4 carbon atoms] by any method which is in itself known for forming an amide, sulphamide, carbamate or urea group without affecting the rest of the molecule, and then, if necessary, reducing the sulphoxide and removing the protective groups.

It is understood that the products which contain a sulpho, sulphonyl or sulphamoyl group are preferably prepared from a product of the general formula (XVb) in which n=0.

Furthermore, if it is desired to prepare a product in which the radical R contains an amino or hydroxyl group, it is necessary to protect these radicals in the reactant used.

If it is desired to prepare a product of the general formula (XV) in which the radical R contains an alkylsulphonylamino, sulphamoylamino, acylamino (substituted or unsubstituted), alkoxycarbonylamino or dialkylureido substituent, the reaction is advantageously out the reaction with the corresponding acid, under the operating conditions described above for use of the acid of the general formula (X).

If it is desired to obtain a product of the general formula (XV) in which R contains a ureido or alkylureido radical, an alkali metal isocyanate or an alkyl isocyanate, respectively, is reacted with the corresponding product of the general formula (XVb), in an aqueous-organic or organic medium (e.g. in tetrahydrofuran), at a temperature between −20° and 60° C.

The reduction and the removal of the protective radicals are carried out under the conditions described above.

V. The thiovinylcephalosporins of the general formula (XV) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by a radical of the general formula (XVIc) or by a hydroxyiminoalkyl or alkoxyiminoalkyl radical, the iminoalkyl part of which contains 2 to 5 carbon atoms, or represents a tetrazol-5-yl radical substituted in the 1-position by a hydroxyiminoalkyl or alkoxyiminoalkyl radical, the iminoalkyl part of which contains 2 to 5 carbon atoms, and $R^o{}_1$ and $R^o{}_2$ have the corresponding definitions, which are addition derivatives of the product of the general formula (XV) in which R is one of the heterocyclic rings mentioned above, substituted by a formylalkyl radical (or its hydrate form), can be obtained from an aldehyde of the general formula:

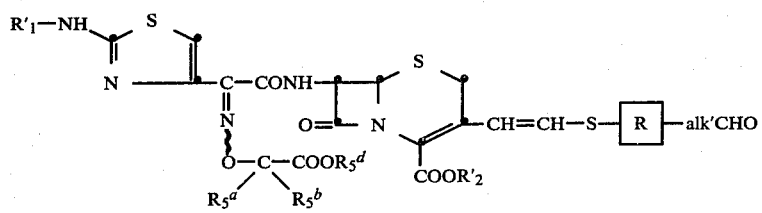

[in which $R^a{}_5$, $R^b{}_5$, $R^d{}_5$, $R'_1$ and $R'_2$ are defined as above and — $\boxed{R}$ —alk'CHO represents a 5,6-dioxo-1-(or 4-)formylalkyl-1,4,5,6-tetrahydro-1,2,4-triazin-3-yl, 1-formylalkyl-1,3,4-(or 1,2,4-)triazol-5-yl, 2-alkoxycarbonyl-1-formylalkyl-1,3,4-triazol-5-yl, 3-alkoxycarbonyl-1-formylalkyl-1,2,4-triazol-5-yl or 1-formylalkyltetrazol-5-yl radical] by the addition respectively of cysteamine, an alcohol, hydroxylamine or an alkoxyamine, in accordance with the methods known for forming addition derivatives of carbonylated groups, this being followed, if necessary, by the removal of the protective radicals.

The reaction is generally carried out in an organic solvent, at a temperature between 20° C. and the reflux temperature of the reaction mixture.

The organic solvents are chosen according to the solubility of the products. If a product of the general formula (XVc) in which $R^d{}_5$, $R'_1$ and $R'_2$ are other than hydrogen is used, solvents such as tetrahydrofuran, acetonitrile, alcohols and ketones are advantageously used. If a product of the general formula (XVc) in which $R^d{}_5$, $R'_1$ and $R'_2$ are hydrogen atoms is used, the reaction is advantageously carried out in solvents such as pyridine, dimethyl sulphoxide or dimethylformamide.

If it is desired to prepare a product of the general formula (XV) in which the radical R contains a substituent of the general formula (XVIc), the reaction is carried out in an acid medium.

VI. The 3-thiovinylcephalosporins of the general formula (XV) in which $R^o{}_2$ represents a radical of the general formula (II), in which $R_6$ and $R_7$ are defined as above, can also be obtained by the esterification of a product of the general formula (XV) in which $R^o{}_2$ represents a hydrogen atom, and in which the amine and acid groups of the substituent in the 7-position have been protected beforehand, by any method which is in itself known for preparing an ester from an acid without affecting the rest of the molecule, this being followed by the removal of the protective groups.

The reaction is carried out in particular under the conditions described above for the preparation of products of the general formula (VII) in which $R_2$ is a radical of the general formula (II).

The products of the general formulae (XIX) or (XIXa) in which n=1 can be obtained by oxidising the corresponding products in which n=0, in accordance with the method described in German Patent Application No. 2,637,176.

The isomers of the products of the general formulae (I), (XV), (XVII), (XVIII), (XIX) or (XIXa) can be separated by crystallisation or by chromatography.

The new products according to the invention and the products of the general formula (XV) can be purified, if appropriate, by physical methods such as crystallisation, chromatography or ultrafiltration.

The cephalosporin derivatives of the general formula (XV), as defined above, and their pharmaceutically acceptable salts possess particularly valuable antibacterial properties. They show a remarkable in vitro and in vivo activity against Gram-positive and Gram-negative germs:

In vitro, they have shown themselves to be active at a concentration of between 0.5 and 10 μg/cc against staphylococcus strains sensitive to penicillin G (*Staphylococcus aureus* Smith) and at a concentration of between 0.01 and 2 μg/cc against *Escherichia coli*, NIJH strain. Furthermore, some of them have been shown to be active at a concentration of between 2 and 125 μg/cc against *Pseudomonas aeruginosa*.

In vivo, they have shown themselves to be active at a daily dose of between 0.5 and 15 mg/kg, administered subcutaneously, against experimental infections caused in mice by *Staphylococcus aureus* Smith (sensitive to penicillin G), and at daily doses of between 0.01 and 10 mg/kg, administered subcutaneously, against experimental infections caused in mice by *Escherichia coli* (NIHJ strain).

Furthermore, the $LD_{50}$ of the products of the general formula (XV) is between 1 g/kg and doses of more than 2.5 g/kg, administered subcutaneously to mice.

The following example shows how the invention can be put into practice. In this example, the products are named according to the nomenclature of Chemical Abstracts. It is understood that all the compounds of the present invention exhibit the stereochemistry given by the partial general formula:

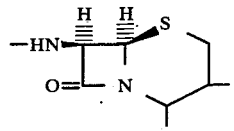

EXAMPLE t-Butoxy-bis dimethylaminomethane (1.9 cc) is added, whilst stirring, to a solution, at 80° C., under nitrogen, of the syn isomer of 2-benzhydryloxycarbonyl-7-{2-[(2-t-butoxycarbonylprop-2-yl)-oxyimino]-2-(2-tritylaminothiazol-4-yl)-acetamido}-3-methyl-8-oxo-5-thia-1-azabicyclo[4.2.0]oct-2-ene (6 g.) in dimethylformamide (64 cc), and the reaction is continued for 15 minutes. The mixture is then poured into a mixture of ethyl acetate (200 cc) and water (200 cc). The organic phase is decanted, washed with water (3×100 cc) and a saturated aqueous solution of sodium chloride (100 cc), dried over sodium sulphate and filtered and the filtrate is concentrated to dryness at 20° C. under 20 mm Hg (2.7 kPa). This yields crude E form of the syn isomer of 2-benzhydryloxycarbonyl-3-(2-dimethylaminovinyl)-7-{2-(2-t-butoxycarbonylprop-2-yl-oxyimino)-2-(2-tritylaminothiazol-4-yl)-acetamido}-8-oxo-5-thia-1- azabicyclo[4.2.0]oct-2-ene (6.5 g) in the form of a hard brown foam.

An aliquot is purified by chromatography on Merck silica gel (0.04–0.06), using a column 4 cm in diameter and 20 cm high, elution being carried out with a cyclohexane/ethyl acetate mixture (65:35 by volume) under a pressure of 40 kPa. Fractions of 50 cm$^3$ each are taken and fractions 14 to 24 are evaporated to dryness. 2-Benzhydryloxycarbonyl-{3-(2-dimethylaminovinyl)-7-2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene, E form, syn isomer (1.2 g) is thus obtained.

Infra-red spectrum (CHBr$_3$), characteristic bands (cm$^{-1}$): 3,400, 3,280, 1,770, 1,720, 1,680, 1,610, 1,525, 1,490, 1,450, 1,370, 940, 750, 735.

Proton NMR spectrum (350 MHz, CDCl$_3$, $\delta$ in ppm, J in Hz): 1.45 (s, 9H, —C(CH$_3$)$_3$); 1.64 and 1.71 (2s, 6H, =N—O—C(CH$_3$)$_2$—); 2.93 (s, 6H, —N(CH$_3$)$_2$); 3.20 and 3.30 (2d, J=14, 2H, —S—CH$_2$—); 5.18 (d, J=4, 1H, —H in the 6-position); 5.71 (dd, J=4 and 9, 1H, —H in the 7-position); 6.61 and 6.82 (2d, J=14, 2H, —CH=CH—S—); 6.88 (s, 1H, H of the thiazole); 6.92 (s, 1H, —COO—CH(C$_6$H$_5$)$_2$); 6.92 (s broad, 1H, —NH—C(C$_6$H$_5$)$_3$); 8.28 (d, J=9, 1H, —CO—NH—).

2-Benzhydryloxycarbonyl-7-{2-[(2-t-butoxycarbonylprop-2-yl)-oxyimino]-2-(2-tritylaminothiazol-4-yl)-acetamido}-3-methyl-8-oxo-5-thia-1-azabicyclo[4.2.0]oct-2-ene, syn isomer, can be prepared in the following way. A solution of phosgene in chlorobenzene (1.3 m), (40 cm$^3$) is added at −10° C. over 30 minutes and with stirring to a solution of 2-(2-t-butoxycarbonylprop-2-yl)-oxyimino-2-(2-tritylaminothiazol-4-yl)-acetic acid (25.58 g), prepared according to Belgian Patent No. 876541 in a mixture of dichloromethane (250 cm$^3$) and dimethylacetamide (13.9 cm$^3$). The mixture is stirred for a further 3 hours at −10° C. and a solution of 7-amino-2-benzhydryloxycarbonyl-3-methyl-8-oxo-5-thia-1-azabicyclo[4.2.0]oct-2-ene (16.29 g) in dichloromethane (250 cm$^3$) is then added drop by drop over 1 hour 15 minutes. After 1 hour 15 minutes at −10° C., the mixture is washed with 2% aqueous sodium bicarbonate solution (200 cm$^3$) and water (200 cm$^3$) and then dried over anhydrous sodium sulphate and concentrated to dryness at 30° C. under 20 mm Hg (2.7 kPa). The residue was chromatographed on a column of Merck silica gel (200 g, 0.05–0.2), the column diameter being 4 cm. Elution was effected with a mixture of cyclohexane and ethylacetate (70:30 by volume) taking fractions of 120 cm$^3$. Fractions 6 to 10 are concentrated to dryness at 30° C. under 20 mm Hg (2.7 kPa). 2-Benzhydryloxycarbonyl-7-[2-(2-t-butoxycarbonylprop-2-yl)-oxyimino-2-(2-tritylaminothiazol-4-yl)acetamido]-3-methyl-8-oxo-5-thia-1-azabicyclo[4.2.0]oct-2-ene, syn isomer (8.5 g), is thus obtained as a yellow foam. The infra-red spectrum of this product (in CHBr$_3$) shows characteristic bands at (cm$^{-1}$): 3,400, 3,270, 1,790, 1,725, 1,685, 1,525, 1,500, 1,450, 1,380, 1,370, 760 and 740.

The products according to the invention can be used in the following manner:

REFERENCE EXAMPLE

A mixture of a solution of the E form of the syn isomer of 2-benzhydryloxycarbonyl-3-(2-dimethylaminovinyl)-7-{2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene (6.45 g) in ethyl acetate (100 cc), and 1 N hydrochloric acid (64 cc), is stirred for 1 hour at 20° C. The organic phase is decanted, washed with water (100 cc), a saturated aqueous solution of sodium bicarbonate (100 cc) and a saturated aqueous solution of sodium chloride (100 cc), dried over sodium sulphate and filtered and the filtrate is concentrated to dryness at 20° C. under 20 mm Hg (2.7 kPa). Crude syn isomer of 2-benzhydryloxycarbonyl-7-{2-[(2-t-butoxycarbonylprop-2-yl)-oxyimino]-2-(2-tritylaminothiazol-4-yl)-acetamido}-3-formylmethyl-8-oxo-5-thia-1-aza-bicyclo[4.2.0]oct-2-ene (4.95 g) is collected in the form of a hard brown foam.

Infra-red spectrum (CHBr$_3$), characteristic bands (cm$^{-1}$): 3,400, 3,270, 2,720, 1,770, 1,725, 1,685, 1,525, 1,495, 1,450, 1,370, 755, 700.

Proton NMR spectrum (350 MHz, CDCl$_3$, $\delta$ in ppm, J in Hz): 1.45 (s, 9H, —C(CH$_3$)$_3$); 1.64 and 1.67 (2s, 6H, (—CH$_3$)$_2$); 3.25 and 3.54 (2d, J=18, 2H, —SCH$_2$—); 3.50 and 3.73 (2d, J=16, 2H, —CH$_2$CHO); 5.10 (d, J=4, 1H, H in the 6-position); 6.06 (dd, J=4 and 9, 1H, H in the 7-position); 6.77 (s, 1H, H of the thiazole); 6.90 (s, 1H, —COOCH<); 8.22 (d, J=9, 1H, —CONH—); 9.58 (s, 1H, —CHO).

p-Toluenesulphonyl chloride (1.31 g) is added to a solution, cooled to 5° C., of the syn isomer of 2-benzhydryloxycarbonyl-7-{2-[(2-t-butoxycarbonylprop-2-yl)oxyimino]-2-(2-tritylaminothiazol-4-yl)-acetamido}-3-formylmethyl-8-oxo-5-thia-1-azabicyclo[4.2.0]oct-2-ene (4.45 g) in pyridine (50 cc). The temperature is left to rise to 20° C. in the course of 30 minutes, the mixture is stirred for 1 hour at 20° C. and poured into iced water (300 cc), the water is decanted and the insoluble pasty product is taken up in ethyl acetate (300 cc). The solution is washed with 1 N hydrochloric acid (100 cc), a saturated solution of sodium bicarbonate (100 cc) and a saturated solution of sodium chloride (100 cc), dried over sodium sulphate and filtered and the filtrate is concentrated to dryness at 20° C. under 20 mm Hg (2.7 kPa). The product thus obtained is used as such for the remainder of the synthesis. This product (1 g) is purified by chromatography on a column of silica gel (0.05–0.2) (20 g) (diameter of the column: 1.7 cm), elution being carried out with an 80/20 (by volume) mixture of cyclohexane and ethyl acetate and 50 cc fractions being collected. Fractions 4 to 12, containing the pure product, are evaporated to dryness under reduced pressure (30 mm Hg; 4 kPa) at 30° C. This yields a mixture of the E and Z forms of the syn isomer of 2-benzhydryloxycarbonylacetamido-7-{2-[(2-t-butoxycarbonylprop-2-yl)-oxyimino]-2-(2-tritylaminothiazol-4-yl)acetamido}-8-oxo-3-(2-tosyloxyvinyl)-5-thia-1-azabicyclo [4.2.0]oct-2-ene (0.43 g) (in proportions—determined by NMR—of 75% of the E form and 25% of the Z form) in the form of a pale yellow solid.

Infra-red spectrum (CHBr$_3$), characteristic bands (cm$^{-1}$): 3,400, 3,260, 1,790, 1,720, 1,680, 1,630, 1,595, 1,580, 1,520, 1,490, 1,450, 1,380, 1,370, 1,190, 1,180, 1,070, 835, 750.

Proton NMR spectrum (350 MHz, CDCl$_3$, $\delta$ in ppm, J in Hz), mixture of E and Z isomers in the proportions 75/25.

E form: 1.45 (s, 9H, —C(CH$_3$)$_3$); 1.62 and 1.67 (2s, 6H, =N—O—C(CH$_3$)$_2$—); 2.48 (s, 3H, —CH$_3$ of the tosyl); 3.42 and 3.50 (2d, J=18, 2H, —S—CH$_2$—); 5.08 (d, J=4, 1H, —H in the 6-position); 6.00 (dd, J=4 and 9, 1H, —H in the 7-position); 6.78 (s, 1H, H of the thiazole); 6.88 (m, 1H, —NH—C(C$_6$H$_5$)$_3$); 6.90 and 6.97

(2d, J=12, 2H, —CH=CH—S—); 6.92 (s, 1H, —COO—CH(C₆H₅)₂); 8.20 (d, J=9, 1H, —CO—NH—). Z form: 6.20 and 6.47 (2d, J=7, —CH=CH—S— Z); 2.45 (s, —CH₃ of the tosyl).

A solution of 90% pure m-chloroperbenzoic acid (0.464 g) in methylene chloride (10 cc) is added dropwise, in the course of 25 minutes, to a solution, cooled to 0° C., of a mixture of the E and Z forms (80% E+20% Z) of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene (3 g) in methylene chloride (50 cc). The mixture is stirred for 1 hour at 0° C., diluted with ethyl acetate (500 cc), washed with a 2% strength solution of sodium bicarbonate (2×100 cc), water (2×100 cc) and a saturated aqueous solution of sodium chloride (100 cc), dried over sodium sulphate and filtered and the filtrate is concentrated to dryness at 20° C. under 20 mm Hg (2.7 kPa). The residue is chromatographed on a column of Merck silica gel (0.06–0.2) (60 g) (diameter of the column: 2 cm, height: 20 cm) and elution is carried out with a cyclohexane/ethyl acetate mixture (70/30 by volume) (1 liter), 60 cc fractions being collected. Fractions 5 to 14 are concentrated to dryness at 20° C. under 20 mm Hg (2.7 kPa) and the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (1.9 g) is collected in the form of a hard yellow foam.

Infra-red spectrum (CHBr₃), characteristic bands (cm⁻¹): 3,380, 1,800, 1,720, 1,680, 1,590, 1,580, 1,510, 1,490, 1,445, 1,375, 1,190, 1,175, 1,070, 730.

Proton NMR spectrum (350 MHz, d₆-DMSO, δ in ppm, J in Hz): 1.37 (s, 9H, —C(CH₃)₃); 1.45 and 1.46 (2s, 6H, —OC(CH₃)₂—); 2.44 (s, 3H, —CH₃ of the tosyl); 3.60 and 4.41 (2d, J=18, 2H, —SCH₂—); 5.06 (d, J=4, 1H, H in the 6-position); 5.96 (dd, J=4 and 9, 1H, H in the 7-position); 6.75 (d, J=13, 1H, —CH=C-HS—); 6.73 (s, 1H, H of the thiazole); 6.93 (s, 1H, —COOCH—); 7.48 and 7.84 (AB-type, 2H, J=9); 8.16 (d, J=9, 1H, —CONH—); 8.73 (s, 1H, —NHC(C₆H₅)₃).

A mixture of the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (6.79 g), dimethylformamide (60 cc), 4-(2,2-dimethoxyethyl)-5,6-dioxo-3-thioxo-perhydro-1,2,4-triazine (1.68 g) and N,N-diisopropylethylamine (1.25 cc) is heated at 60° C. for 4 hours, whilst stirring and under nitrogen. The mixture is diluted with ethyl acetate (250 cc), washed with water (3×125 cc) and a saturated solution of sodium chloride (2×125 cc), dried over sodium sulphate and filtered and the filtrate is concentrated to dryness at 20° C. under 20 mm Hg (2.7 kPa). The residue obtained after this treatment is chromatographed on a column of Merck silica gel (0.06–0.2) (125 g) (diameter of the column: 3 cm, height: 43 cm). Elution is carried out with a 50/50 (by volume) cyclohexane/ethyl acetate mixture (1.5 liters) and ethyl acetate (1 liter), 100 cc fractions being collected. Fractions 16 to 21 are concentrated to dryness at 25° C. under 20 mm Hg (2.7 kPa) and this yields the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (5.5 g) in the form of a hard brown foam.

Infra-red spectrum (CHBr₃), characteristic bands (cm⁻¹): 1,800, 1,720, 1,690, 1,585, 1,510, 1,495, 1,445, 1,370, 1,080, 1,060, 1,040, 940, 750, 700.

Proton NMR spectrum (350 MHz, d₆-DMSO, δ in ppm, J in Hz): 1.35 (s, 9H, —C(CH₃)₃); 1.44 and 1.45 (2s, 6H, =N—O—C(CH₃)₂); 3.32 (s, 6H, (—OCH₃)₂); 3.65 and 4.36 (2d, J=18, 2H, —S—CH₂—); 3.95 (d, J=5, 2H, >N—CH₂—); 4.56 (t, J=5, 1H,

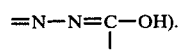

5.09 (d, J=5, 1H, —H in the 6-position); 5.95 (dd, J=5 and 9, 1H, —H in the 7-position); 6.78 (s, 1H, —H of the thiazole); 7 (s, 1H, —COO—CH(C₆H₅)₂); 7.02 and 7.1 (2d, J=16, 2H, —CH=CH—S—); 8.23 (d, J=9, 1H, —CO—NH—); 8.73 (s, 1H, —NH—C(C₆H₅)₃); 12.65 (s, 1H, =N—NH—CO— or

=N—N=C—OH).
      |

A solution of the E form of the syn isomer of 2-benzhydryloxycarbonyl-7-{2-[(2-t-butoxycarbonylprop-2-yl):oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (5.37 g) in methylene chloride (45 cc) and N,N-dimethylacetamide (1.79 cc) is treated with phosphorus trichloride (0.79 cc), at −5° C., for 1 hour 30 minutes, whilst stirring. After the reaction mixture has been washed with a 2% strength solution of sodium bicarbonate and evaporated to dryness, the residue is dissolved in the minimum amount of methylene chloride, the solution is chromatographed on a column of Merck silica gel (0.06–0.2) (80 g) (dimeter of the column: 2 cm, height: 20 cm) and elution is carried out with a 40/60 (by volume) cyclohexane/ethyl acetate mixture (250 cc) and a 30/70 mixture (1.5 liters), 100 cc fractions being collected. Fractions 5 to 14 are concentrated to dryness at 25° C. under 20 mm Hg and this yields the E form of the syn isomer of 2-benzhydryloxycarbonyl-7-{2-[(2-t-butoxycarbonylprop-2-yl)-oxyimino]-2-(2--tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (4.02 g) in the form of a hard, light brown foam.

Infra-red spectrum (KBr), characteristic bands (cm⁻¹): 1,790, 1,720, 1,690, 1,585, 1,520, 1,495, 1,450, 1,370, 1,080, 940, 750, 700.

Proton NMR spectrum (350 MHz, d₆-DMSO, δ in ppm, J in Hz): 1.37 (s, 9H, —C(CH₃)₃); 1.42 (s, 6H, =N—O—C(CH₃)₂—); 3.31 (s, 6H, (—OCH₃)₂); 3.64 and 3.89 (2d, J=18, 2H, —S—CH₂—); 3.95 (d, J=5, 2H, >N—CH₂—); 4.56 (t, J=5, 1H,

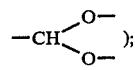

5.26 (d, J=4, 1H, —H in the 6-position); 5.77 (dd, J=4 and 9, 1H, —H in the 7-position); 6.71 (s, 1H, —H of the thiazole); 6.90 and 7.03 (2d, J=16, 2H, —CH=

CH—S—); 6.97 (s, 1H, —COO—C<u>H</u>(C6H5)2); 8.80 (s, 1H, —N<u>H</u>—C(C6H5)3); 9.39 (d, J=9, 1H, —CO—NH—); 12.66 (s, 1H, =N—NH—CO— or =N—N=C—OH).

A solution of the E form of the syn isomer of 2-benzhydryloxycarbonyl-7-{2-[(2-t-butoxycarbonylprop--2-yl)-oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (3.89 g) in trifluoroacetic acid (39 cc) is stirred at 20° C. for 20 minutes. It is concentrated to dryness at 20° C. under 0.05 mm Hg (0.007 kPa), the residue is taken up in diethyl ether (100 cc) and the solution is stirred for 10 minutes and filtered. The solid obtained is treated with formic acid (80 cc), at 50° C., for 45 minutes, water (16 cc) is added and the mixture is kept at 50° C. for 30 minutes and concentrated to dryness at 20° C. under 0.05 mm Hg (0.007 kPa). The residue is taken up in acetone (3×150 cc), each solution being evaporated at 20° C. under 30 mm Hg (4 kPa), and the residue is heated under reflux in acetone (100 cc), whilst stirring. The mixture is filtered and the E form of the syn isomer of 7-{2-(2-aminothiazol-4-yl)-2-[(2-carboxyprop-2-yl)-oxyimino]-acetamido}-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo-[4.2.0]oct-2-ene (2.15 g) is collected in the form of a yellow powder.

Infra-red spectrum (KBr), characteristic bands (cm$^{-1}$): 3,400, 3,300, 3,200, 2,200, 1,780, 1,720, 1,685, 1,585, 1,540, 1,000.

Proton NMR spectrum (350 MHz, CF3COOD, δ in ppm, J in Hz): 1.85 and 1.86 (2s, 6H, —CH3); 3.90 (s broad, 2H, —SCH2—); 5.20 (s, 2H, —C<u>H</u>2CHO); 5.40 (d, J=4, 1H, H in the 6-position); 6.12 (d, J=4, 1H, H in the 7-position); 7.23 and 7.76 (2d, J=16, 2H, —CH=CH—); 7.50 (s, 1H, H of the thiazole); 9.73 (s, 1H, —CHO).

We claim:

1. A 3-vinylcephalosporin of the formula:

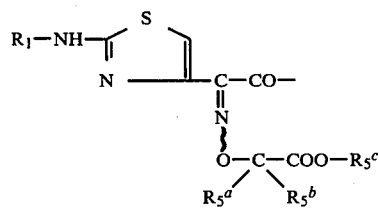
(I)

in the form of a bicyclooct-2-ene or bicyclooct-3-ene in which the substituent in the 3-position of the bicyclooctene is in the E or Z form or a mixture thereof; and the imine group of the substituent in the 7-position is in the syn or anti form or a mixture thereof; wherein $R^a_5$ and $R^b_5$, which are identical or different, represent hydrogen atoms or alkyl radicals, or together form an alkylene radical containing 2 or 3 carbon atoms; $R^c_5$ represents an acid-protecting radical; $R_1$ represents an amine-protecting radical; $R_2$ represents a radical which can easily be removed by an enzymatic method having the formula:

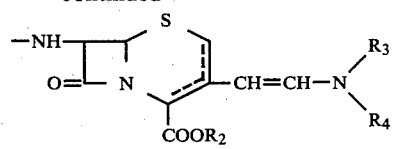

-continued

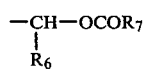
(II)

in which $R_6$ represents a hydrogen atom or an alkyl radical and $R_7$ represents an alkyl radical or the cyclohexyl radical, or $R_2$ represents a methoxymethyl, t-butyl, benzhydryl, p-nitrobenzyl or p-methoxybenzyl radical; and the symbols $R_3$ and $R_4$, which are identical or different, represent alkyl radicals, which are unsubstituted or substituted by a hydroxyl, alkoxy, amino, alkylamino or dialkylamino radical, or phenyl radicals, or together form, with the nitrogen atom to which they are attached, a saturated heterocyclic ring of 5 or 6 ring members, which may contain another hetero-atom chosen from nitrogen, oxygen and sulphur, and is unsubstituted or substituted by an alkyl radical, the above-mentioned alkyl portions or radicals being (unless otherwise mentioned) straight or branched and containing 1 to 4 carbon atoms.

2. A 3-vinylcephalosporin according to claim 1, in which the protective radical $R^c_5$ is chosen from methoxymethyl, t-butyl, benzhydryl, benzyl, nitrobenzyl and p-methoxybenzyl.

3. A 3-vinylcephalosporin derivative according to claim 1, in which the protective radical $R_1$ is chosen from t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl and trifluoroacetyl.

4. 2-Benzhydryloxycarbonyl-3-(2-dimethylaminovinyl)-7-{2-(2-t-butoxycarbonyl-prop-2-yloxyimino)-2-(2-tritylaminothiazol-4-yl)-acetamido}-8-oxo-5-thia-1-azabicyclo[4.2.0]oct-2-ene.

* * * * *